United States Patent [19]

Tomlinson

[11] Patent Number: 5,022,406
[45] Date of Patent: Jun. 11, 1991

[54] MODULE FOR DETERMINING DIFFUSING CAPACITY OF THE LUNGS FOR CARBON MONOXIDE AND METHOD

[76] Inventor: Harold W. Tomlinson, 57 Commonwealth Dr., Glenmont, N.Y. 12077

[21] Appl. No.: 455,263

[22] Filed: Dec. 22, 1989

Related U.S. Application Data

[63] Continuation-in-part of Ser. No. 226,562, Aug. 1, 1988, abandoned, which is a continuation of Ser. No. 916,306, Oct. 7, 1986, abandoned.

[51] Int. Cl.$^5$ .............................................. A61B 5/08
[52] U.S. Cl. ................................. 128/719; 128/725; 128/738
[58] Field of Search ............... 128/719, 730, 716, 718, 128/725

[56] References Cited

U.S. PATENT DOCUMENTS

| | | | |
|---|---|---|---|
| 3,507,146 | 4/1970 | Webb | 128/719 |
| 3,759,249 | 9/1973 | Fletcher et al. | 125/719 |
| 3,785,370 | 1/1974 | Richards et al. | 178/719 |
| 3,824,079 | 7/1974 | Venema | 128/719 |
| 4,067,320 | 1/1978 | Olsson et al. | 128/719 |
| 4,178,919 | 12/1979 | Hall | 128/719 |
| 4,202,352 | 5/1980 | Osborn | 128/719 |
| 4,535,780 | 8/1985 | Gur et al. | 128/719 |
| 4,648,396 | 3/1987 | Raemer | 128/719 |
| 4,872,208 | 2/1986 | Cutler et al. | 128/719 |
| 4,881,942 | 4/1986 | Ogura et al. | 128/719 |

OTHER PUBLICATIONS

"Single Breath Carbon Monoxide Diffusing Capacity", ATS, Am. Rev. Respir Dis 1987; 136:1299–1307.
Hamilton, L., "Acoustic Helium Analyzer for Closing Volume Measurement", 1976, pp. 911–915.
Hauck, H., "Computer-Aided Measuring System for Investigating the Uptake of Carbon Monoxide Via the Respiration," Biomed Techn. 2(1979), 82–88.

*Primary Examiner*—Randall L. Green
*Assistant Examiner*—K. Reichle
*Attorney, Agent, or Firm*—Dann, Dorfman, Herrell and Skillman

[57] ABSTRACT

An apparatus for introducing test gas commonly containing an inert gas and carbon monoxide to a patient through a mouthpiece which, in turn, is attached to a sample chamber within which are arranged sensors enabling measuring of carbon monoxide, carbon dioxide, an inert gas or other gases. Valving permits the test gas to be inhaled by the patient and then exhaled into the chamber. Further valving at the outlet of the chamber permits evacuation through a gas volume measuring device after measurements within the chamber have been completed. Sample chambers may be of various shapes but preferred forms are essentially linear or closed loop arrangements.

23 Claims, 4 Drawing Sheets

| CO SENSOR ON ENTIRE TIME | | FLUSH/ CALIBRATE | DLCO PROCEDURE | | ANALYZE | GAS FLUSH | AIR FLUSH | END |
|---|---|---|---|---|---|---|---|---|
| DEMAND VALVE | FL. OP. | | | | | | | |
| EXHAUST VALVE | OP. CL. | | | | | | | |
| MOUTHPIECE VALVE | OP. CL. | | | | | | | |
| REBREATH VALVE | OP. CL. | | | | | | | |
| TURBINE | ON OFF | | | | | | | |
| PNEUMOTACH VALVE | OP. CL. | | | | | | | |
| HELIUM SENSOR | ON OFF | | | | | | | |
| $CO_2$ SENSOR | ON OFF | | | | | | | |
| PATIENT PROCEDURE | | GAS FLUSH CALIBRATE | | | ANALYZE | | | |
| INPUTS | | He,CO,$CO_2$,Temp | TEMP/FLOW | | He,CO,$CO_2$, Temp | SOLVE DLCO | FOR VA, | Fa $CO_0$, |

FIG. 4

MODULE FOR DETERMINING DIFFUSING CAPACITY OF THE LUNGS FOR CARBON MONOXIDE AND METHOD

This is a continuation-in-part application of Ser. No. 226,562, filed Aug. 1, 1988, which is a continuation of application Ser. No. 916,306, filed Oct. 7, 1986, both now abandoned.

The present invention relates to an apparatus for performing gas measurements required for determining the diffusion capacity of the lungs for carbon monoxide and the method of using the same. More specifically, the present invention relates to such a diffusion module which can be made lightweight and portable and eliminates components as well as processing steps involved with prior equipment.

BACKGROUND OF THE INVENTION

The primary purpose of the lungs is to transfer oxygen into and carbon dioxide out from the blood. Diagnostic testing for lung disease is called pulmonary function testing. Most commonly, this testing is done on three categories of lung function, the mechanics of the lungs or the ability of the lungs to move air in and out, the measurement of lung volumes and the testing for the ability of the lungs to transfer oxygen into and carbon dioxide out from the blood, or diffusing capacity. Measuring the diffusing capacity for oxygen is difficult because of the inability to measure the mean partial pressure of oxygen in the pulmonary capillaries. Carbon monoxide (CO) on the other hand diffuses rapidly into the blood and attaches to the hemoglobin, which has a great affinity for CO. Because of this affinity, the test commonly employed uses CO and is called the diffusing capacity test for carbon monoxide or DLCO.

DLCO requires equipment designed to perform the test according to specifications of the American Thoracic Society (ATS); the latest version of this specification was adopted March 1987. This equipment must provide a means for a measured volume of test gas comprised of CO, air and an inert gas such as helium to be inhaled by the patient. The gas is held in the lung for 10 seconds and then exhaled. CO and the helium concentrations are known or measured before and measured after breathhold. The CO concentration is reduced by the amount diffused into the blood. The helium does not diffuse, but is diluted by the residual volume of the lung and thus reduced in concentration. Other inert gases may be used such as argon.

In the prior art the DLCO equipment has divided the expired sample into three parts. The first part, 750 ml, is discarded because it comes from the anatomical dead space in the lung. The next 500 ml to 1000 ml is collected in a sample collection bag. The remainder of the exhaled gas is also discarded. The sample collected in the bag is then transferred to gas analyzers, one for CO and one for helium. Scrubbers to remove water vapor and carbon dioxide ($CO_2$) as interferences in the gas analyzers may also be used.

The measurement of the mechanics of the lung is done with a volume spirometer or pneumotach. Lung volumes can be measured with various equipment. Spirometry has been known and used in some forms in diagnosis of lung disorders for a long time. However, what can be learned from spirometry alone is limited. Measurement of pulmonary diffusing capacity has been understood since about 1915, but was not a practical tool for many years. Equipment for clinical use of pulmonary diffusing capacity was developed in the 1950's. Since that time, such equipment has been used in hospital pulmonary function labs to assist in the differential diagnosis of lung disease. Automatic valve sequencers developed early in the 1970's made differential CO measurements less difficult and more reproducible. These sequencers made handling of the inhaled gas and the exhaled sample more automatic. However, the same pieces of equipment for gas analysis and scrubbing are still required by equipment today.

Interstitial lung diseases, such as asbestosis, coal workers pneumoconiosis, and silicosis, caused by the inhalation of inorganic dusts, can be diagnosed by such equipment. Annual spirometry is now required by law for workers exposed to those enumerated and many other diseases produced by inorganic dusts. However, unavailability of portable, easy-to-use devices for testing diffusion capacity has made impractical enactment of the legislation requiring use of such devices.

It is widely recognized that clinical screening of patients with interstitial lung disease would be enhanced by diffusion capacity testing. Such testing would much more readily demonstrate a significantly impaired gas exchange in many patients who have no significant defect in the mechanics of breathing, as indicated by the spirometer. Furthermore, many of these patients have normal chest X-rays. Therefore, testing for diffusion capacity of the lungs for carbon monoxide is the only objective evidence of lung disease. Such testing is rapid and noninvasive. If the equipment were more readily available, especially in the field, far better testing for lung disease could be accomplished.

The long time availability of equipment for determining diffusion capacity for carbon monoxide has been limited to special clinical installations because heretofore the equipment has been heavy and bulky, complex and usually quite expensive. Also, prior equipment has often required the collection of a sample of expired gas followed by the transfer of the sample or parts thereof to discreet gas analysis equipment, one for carbon monoxide and one for helium. Transfer of the sample has required a pump or some other motor driven device, although it could be done by a hand syringe. The various steps take technician time. It is alternatively possible to use a gas chromatograph, an additional expensive equipment, to identify the gases. Therefore, these techniques have been too expensive for general use. In addition, the involvement of many mechanical and electronic components has increased the potential for malfunction. This same complexity has tended to make the equipment heavy so that, as a practical matter, it must be used at one place.

THE NATURE OF THE PRESENT INVENTION

The present invention depends upon the use of a predetermined gas mixture, such as so-called DLCO gas which is an essentially standard gas mixture which contains fixed parts of air, carbon monoxide and an inert gas such as helium. The gas is inhaled by the patient in the single breath method, taking as deep a breath as possible. The carbon monoxide in the mixture is preferentially diffused through the lungs and attaches to the hemoglobin in the pulmonary capillaries. The inert gas, such as helium, does not diffuse through the lungs at all. However, it infiltrates the lungs and mixes thoroughly within the lung space. When the mixture is exhaled after a predetermined amount of time, the gases exhaled have a different concentration. The carbon monoxide will be reduced by the amount that has been diffused through the lungs and this will be an indicator of the amount of carbon monoxide which is able to pass through the lungs or, conversely, the amount that is kept out by a deteriorated lining in the lungs. Thus, the amount of residual carbon monoxide as compared to the original would be an indicator of the extent of lung damage. The concentration of helium that is breathed out will be less than the concentration of helium breathed in because the lungs are never able to exhale all of the gases within the lungs and, in this way, the proportion of helium is breathed out, through dilutions as compared to what was breathed in, will be an indication of residual lung volume, a measurement necessary to determine diffusing capacity.

The present invention provides an apparatus for measurement of the diffusing capacity of the lungs for carbon monoxide. The gas collection and measurement apparatus is self-contained. It employs techniques and components which enable measurements to be made within the system but without adding undue weight such that, in fact, the system may be made portable. This system is also relatively inexpensive so that it may be available for use on a wide spread basis, including in the offices of physicians. It is small and easily storable, and even portable, so that the module may be carried from place to place for public screening in high risk areas. Public health uses also become possible because adequate funding is not so difficult.

While evaluation of results may best be performed by a physician, use of the apparatus does not require a physician and requires minimum training of the operating technician. Tests may be performed outside the presence of a physician without impairment of the results or without danger to the patient for later screening and evaluation by a physician.

The present invention provides a process or method of testing for diffusion capacity of the lungs for carbon monoxide. The system preferably includes means for automatically cycling the system through various steps corresponding to the method, thereby providing more precise timing and control of the process than when controlled by human manipulation.

More specifically, the apparatus of the present invention employs a rigid sample chamber. Said chamber has sound transducers fixed within said chamber at a fixed spacing along a flow path therethrough with means to energize at least one of said transducers for the generation and modulation of sound and another for the detection of transmitted sound. Means is connected to the transducers to provide the energy input to and the signal output from the respective transducer and to process data therefrom. An infrared source and an infrared detector are also spaced apart in the chamber to measure carbon dioxide. Sensors for measuring carbon monoxide and temperature are located within the chamber. A flow measurement device is located in the rebreath valve. A mouthpiece for coupling the patient to the apparatus is connected to the chamber and permits input of expired gas from the lungs of a patient under test. A valve for providing a test gas, such as $D_LCO$ gas, and means permitting tanks of such gas to be attached to the system are required. Valve means at the opposite end of the chamber for directing flows to exhaust gases and means to measure the volume of gases exhausted complete equipment of the invention.

Advantageously, automatic computation and readout are possible. Computer means coupled, respectively, to the $CO_2$ and CO detectors, sound signals, volume measurement and temperature devices provide outputs directly calibrated in terms of gas concentrations and volume.

For a better understanding of the present invention, reference is made to the accompanying drawings in which:

FIG. 4 is a time sequence diagram showing the operation of various valve and system components with patient interaction superimposed for the system in FIG. 2.

The apparatus of the present invention relates to a module to perform gas concentration measurements required for determining diffusing capacity of lungs for carbon monoxide. The DLCO gas supply containing known predetermined amounts of carbon monoxide and helium is connectable to the system by suitable valving. The valving can shut off the gas supply, and the mouthpiece is, in turn, opened to the closed chamber. The chamber may be closed except for the input from the mouthpiece but also must be opened so as to allow the expired gas to be exhausted through a valve after passing through a pneumotach or into a spirometer, at the opposite end of the chamber. The chamber preferably contains sensors for detecting amounts of carbon monoxide, carbon dioxide and helium and means for causing mixing of the gases. The chamber may also contain sensors for other types of gases used in the measurement of lung function such as acetylene, freon 22, argon and neon. Acetylene or freon 22 are tissue and plasma soluble and when added to the DLCO gas mixture allows the measurement of pulmonary blood flow in a single breath DLCO maneuver. Argon or neon could be substituted for helium.

Figure 1:
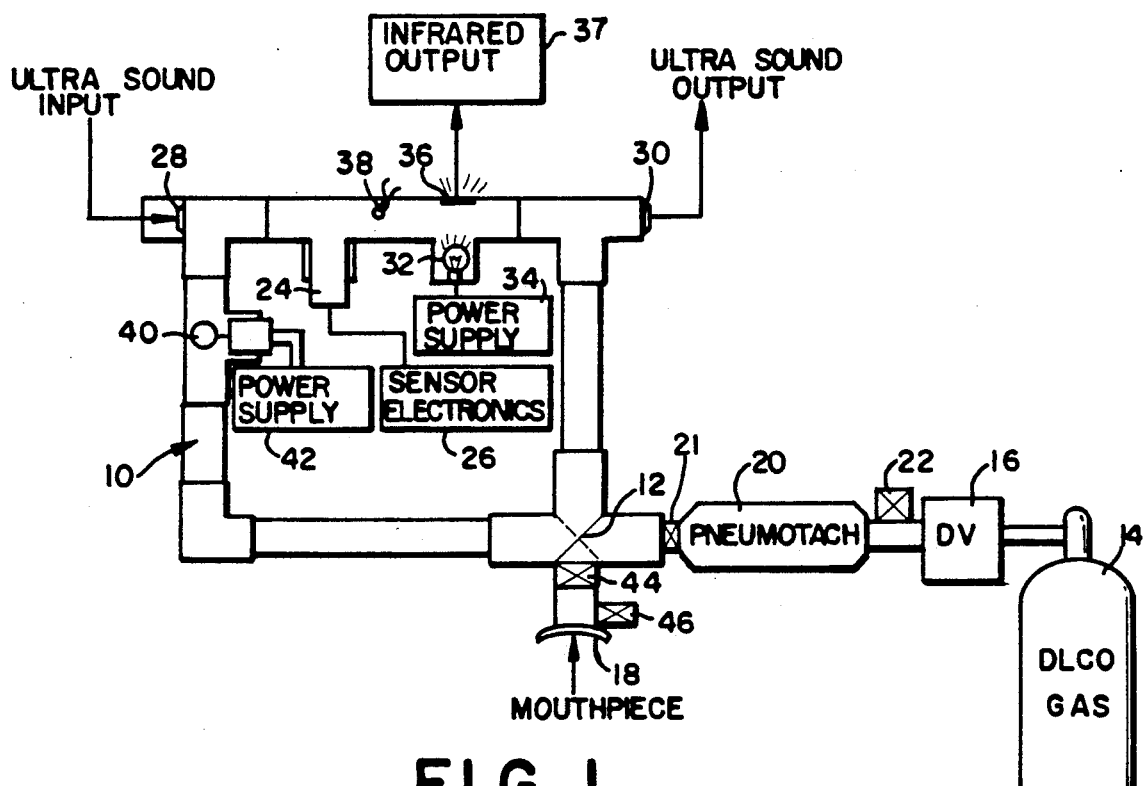
FIG. 1 is a diagrammatic and somewhat schematic plan view of a preferred form of diffusion test apparatus in accordance with the present invention combined with standard accessories and ready for use.

FIG. 1 shows a preferred closed loop system in accordance with the invention. In this system a rigid, fixed volume sample collection chamber 10 is provided. Valve means 12 is provided to allow the introduction of DLCO gas from supply 14 to the patient through demand valve 16, pneumotach 20 and mouthpiece 18 in one position of the valve 12. In the other position of valve 12, the patient exhales through the mouthpiece around the loop of chamber 10 and valve 12 also allows the exhaust thereof through pneumotach 20, a gaseous volume measuring device, and exhaust valve 22. Within the chamber are various gas sensing means. In particular, there is an electrochemical sensor 24 for carbon monoxide provided with its own sensor electronics 26. Also within the chamber 10, separated by a straight line path, are ultrasound transducer 28 and an ultrasound receiver 30. Also separated by a shorter straight line path within the chamber are infrared source 32 fed by power supply 34 and infrared receiver 36 which may employ an infrared band pass filter in its output 37. A thermocouple 38 or other temperature measuring device is placed in the region of one of the other sensors. A mixing device or turbine 40 driven by power supply 42 is provided in the chamber 10 before the measurement equipment.

In use, until the mouthpiece valve 44 is opened, the patient breathes the atmospheric air through rebreathe valve 46. When valve 44 is opened, the DLCO gas from supply 14 is available to be breathed in through the mouthpiece 18 via demand valve 16 and pneumotach 20 when diverter valve 12 in its solid line position. The diverter valve is then switched to its dashed line position, the exhaust valve is opened, following which, after holding his breath, the patient breathes out through the sample chamber 10, the pneumotach 20 and exhaust valve 22. The pneumotach valve 21 remains open to allow expiration. The washout volume plus the volume of the sample chamber is measured by the pneumotach 20 as it passes through pneumotach 20 and out exhaust valve 22. The pneumotach valve 21 closes in conjunction with valve 44 to collect the sample. Rebreath valve 46 opens to allow the balance of the expirate after sample collection to be passed out to atmosphere. The pneumotach valve 21 remains closed to seal off the sample chamber 10 from the pneumotach 20. The closed loop chamber allows mixing of the expirate by turbine 40.

The basic apparatus of FIG. 1 permits measurement of helium and carbon monoxide remaining in the exhaled DLCO test gas. Expired breath samples are tested for carbon monoxide, carbon dioxide and helium during the test for lung diffusion by either a batch method, continuously, or consecutively in a pre-set sequence of timed measurements as the sample passes through the sample chamber, without any transfer of the gas sample to discrete gas analyzers or separation by gas chromatograph.

The device includes a rigid elongated test chamber. The chamber may be conveniently made, as represented, of lightweight resinous tubular plumbing parts of suitable length and volume to accommodate a predetermined part of the expirate gases of the patient under test using the technique of the present invention. The construction is designed to keep the device as small, compact and portable as possible. The device has no sample collection bags, no vacuum pumps, no scrubbers and no discrete gas analysers. In the embodiment disclosed, the tubing is configured most easily into a linear section and may provide a loop using elbows to form a shape. Internally, the tubing parts are conveniently of generally circular cross-section.

Figure 2:
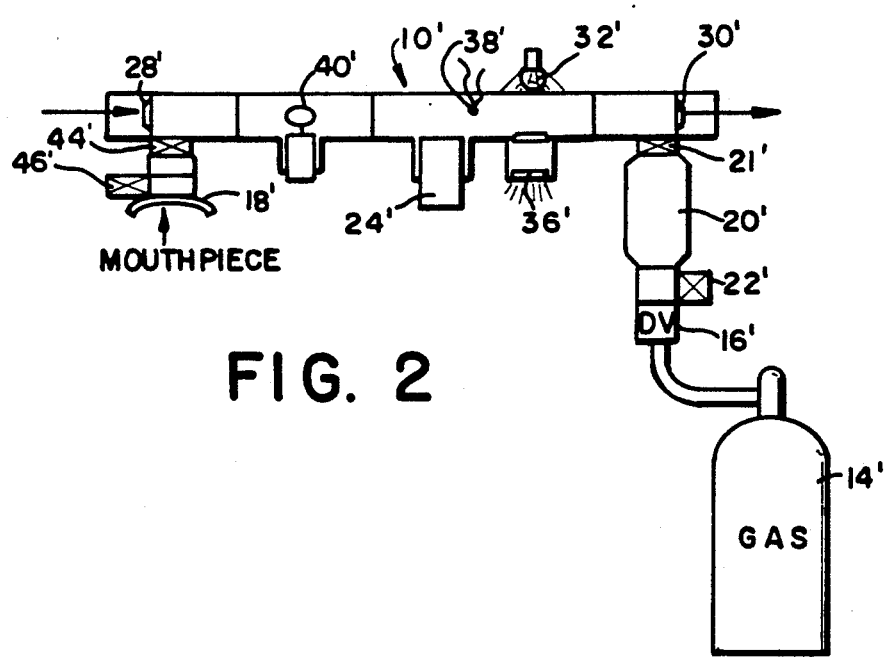
FIG. 2 is a similar view of another preferred form of the apparatus of the invention.

FIG. 2 shows another preferred variation on the module and system of claim 1 wherein the sample chamber is a linear chamber 10' instead of a closed loop. A four-way valve is not required as in the embodiment of FIG. 1 but the gas supply 14' is connected through a demand valve 16' and pneumotach valve 21', through the chamber, to the mouthpiece 18' through a mouthpiece valve 44'. When mouthpiece valve 44' is closed, the patient using the mouthpiece 18' can breathe through the rebreathe valve 46'. After gas has been breathed in through the mouthpiece and held for a brief term in time in the patient's lungs, it is then breathed out through the mouthpiece and through the chamber 10' back through the pneumotach 20' which measures the volume of gas expired and out to atmosphere through exhaust valve 22'. Mouthpiece valve 44' and pneumotach valve 21 are closed after the preset volume has passed through the chamber, thus isolating and trapping the exhaled sample. Within the chamber 10' at opposite ends thereof along a linear path are arranged an ultrasound transducer 28' and a ultrasound receiver 30'. Likewise, there is provided across the linear path an infrared source 32' and an infrared detector 36'. Also along the path is a CO detector 24'. A thermocouple 38' is also provided. A mixing turbine 40' is also provided in this case.

The procedure begins by having the patient put the mouthpiece in his mouth with all valves closed except the rebreath valve 46'. He exhales completely and on signal, the rebreath valve 46' closes and mouthpiece valve 44', pneumotach valve 21' and exhaust valve 22' open. The patient inhales and then exhales through the mouthpiece 18' and the entire system. The pneumotach 20' measures the expired volume and when the volume of the sample chamber and the volume of the anatomical dead space (washout volume) have passed through pneumotach 20', rebreath valve 46' opens, mouthpiece valve 44' and pneumotach valve 21' close, trapping the next volume of expired breath in the space of the sample chamber between mouthpiece valve 44' and pneumotach valve 21'. Immediately following the sample collection, the turbine 40' turns on for sufficient time to mix the gases in the sample chamber. Turbine 40' turns off and the $CO_2$ concentration of the breath sample is measured either by use of the infrared $CO_2$ sensor 32'-36', or by use of the ultrasound transducers 28' and 30', located at either end of the sample chamber. This maneuver can also serve as a practice maneuver for the patient.

Standard test gas is attached to the gas delivery system, normally through a demand valve 16' which permits the operator to introduce gas to the system through a flush configuration ("FL." in FIG. 4) by pressure from the gas supply tank and also allows the patient to breath in as much gas as he can through the demand valve with no resistance in the normal operating configuration ('OP." in FIG. 4). When the system is flushed with gas, the helium concentration of the gas is measured using the ultrasound transducers 28' and 30' and the CO concentration is measured using the CO sensor 24'. The patient then goes back on the mouthpiece and breathes normally through rebreath valve 46' with mouthpiece valve 44' still closed with the test gas in the sample chamber. The patient then exhales through the rebreath valve 46' completely and on signal, the rebreath valve 46' closes and mouthpiece valve 44' and pneumotach valve 21' open. The patient inhales rapidly and completely, sucking the test gas from the supply tank through demand valve 16', pneumotach 20', sample chamber 10', mouthpiece valve 44' and mouthpiece 18'. Pneumotach 20' measures the inspired volume. When flow has stopped, all valves that were open are closed. This helps the patient hold his breath, which he does for nominally 10 seconds, timed automatically with the valve closing. After breath hold, mouthpiece valve 44', pneumotach valve 21' and exhaust valve 22' open and the patient exhales rapidly. The pneumotach 20' measures the expired volume and after the volume of the sample chamber 10' and washout volume have passed the pneumotach 20', pneumotach valve 21', mouthpiece valve 44' and exhaust valve 22' close and rebreath valve 46' opens, allowing the balance of the expirate to be passed to atmosphere through rebreath valve 46'. Thus the volume of the sample chamber is filled with a proper expired sample. The turbine 40' turns on again briefly to mix the gases in the sample chamber 10' and then shuts off. The helium concentration of the sample is measured using the ultrasound transducers 28' and 30'. The CO concentration is measured using the CO sensor 24'. These values are fed to the computer for analysis. The patient comes off the mouthpiece as soon as his expiration is complete. Gas is flushed through the system to ready it for the next test.

It will be understood by those skilled in the art that the apparatus of FIG. 1 and FIG. 2 can be used interchangably, with certain advantages accruing through the longer loop path, and in each case the object of the construction of the sample chamber is to provide zero dead space and to make the path internal of the chamber as smooth as possible.

It can be seen that the gas supply and the lungs are fluidiually connected through the sample chamber so that a single, in-line system is used to deliver the gas to the lungs, separate the expired sample into its three parts, saving the proper sample and discarding those sample portions not needed, all in the same path for both directions of gas flow.

Figure 3:
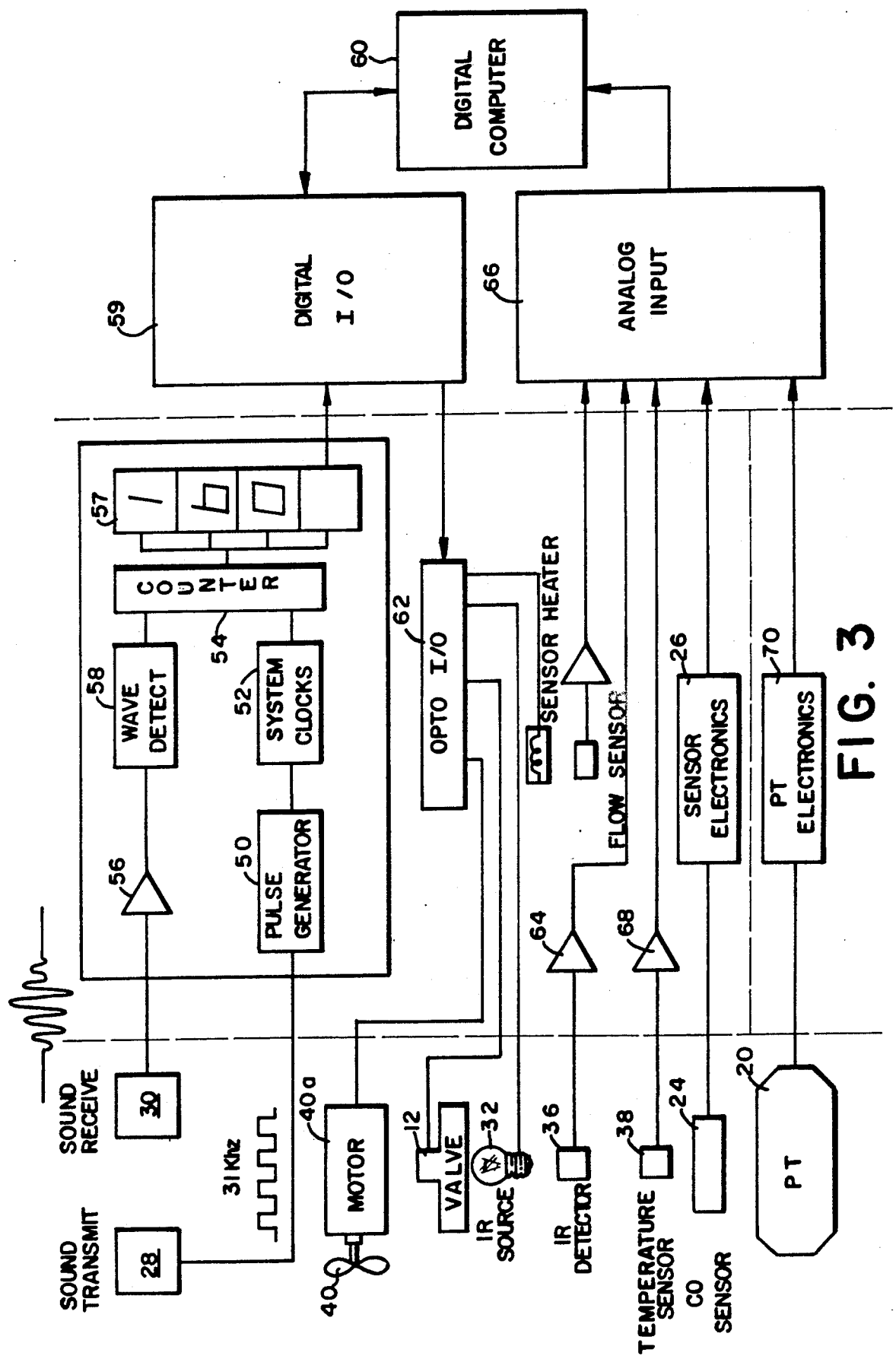
FIG. 3 is a simplified schematic diagram showing connection of the various components to a system computer.

FIG. 3 shows the various active elements of the system of FIG. 1. In a system diagram suggesting how they may be coordinated, the ultrasound elements 28 and 30 are used for measuring helium content within the chamber. They are separated preferably by a straight line path through the gaseous contents. Typically the sound transmitter responds to a high frequency pulse generator 50 which puts out a sound wave which may be at 31 kilohertz, for example. When the wave is transmitted, the system clock 52 is synchronized and provides an output to counter 54 starting a count. When the high frequency sound is received at receiver 30, it is amplified in amplifier 56 fed to a wave detector 58 and, thence, to counter 54 where it signals the end of the count. A register 57, which may include display, stores the count and feeds it to a digital input/output processor 59 and ultimately to digital computer 60 which contains programming as well as input information about gas constituents. The output from the digital input/output device 59 can go to opto input/output 62, which is more realistically a series of controlled power supplies and actuators which are switched on and off in accordance with the program. This is true of the motor 4a driving the turbine. It is true of the four way valve 12 and other valves which must be actuated and which are intended to be represented schematically by showing one valve by way of example. Each valve, in turn, is operated in accordance with programming of the system. It is also true of the IR source, which is turned on and off at the frequency required at the IR detector.

The infrared detector, as shown in FIG. 3, is provided with an amplifier 64 which feeds analog input/digital output device 66 which makes conversion to digital output for the digital computer 60. Temperature sensor 38 is similarly treated and its output signal is amplified by amplifier 68 before being fed to the analog to digital converter 66. The carbon monoxide sensor 24 feeds sensor electronics 26 and its analog output is fed to analog to digital converter 66 for conversion to digital form for the computer 60. The pneumotach 20 feeds an output to pneumotach electronics 70 which, again, puts an analog input into analog to digital converter 66 so that it can be converted to digital form for use by the digital computer.

The digital computer 60 is a central processing and control unit which may also receive manual inputs from a terminal of barometric pressure, patient data and other procedure controlling parameters. The central processing unit, in turn, regulates inputs, such as for valve control, and outputs, such as display, printing and interface with a DLCO supply at its input and with digital input/output device 59 and analog input device 66 from which DLCO sensor readings and volume measurements can be received.

The ultrasound output ultimately provides a solution for the helium content in the gases. The carbon dioxide content is determined by the infrared detection. In some instances, infrared technology can also be used to measure carbon monoxide.

Means may be provided to saturate the inspired gas sample with water vapor prior to entering the sample chamber so that the effects of water vapor are common to the test gas before and after entering the lungs. Means may also be provided to keep the sample temperature above the dew point of the sample to prevent condensation of the water vapor. A commercial CO measuring device is used. The infrared (IR) measurement is correlated to carbon dioxide concentration and the sound velocity measurement is correlated to helium concentration. Carbon dioxide is used as a correction factor in the calculation of helium concentration. The helium and carbon monoxide concentrations are held in the computer as FiHe (inspired helium concentration) and FiCo (inspired carbon monoxide concentration).

The readings from the expired gas sample are held in the computer as $FaHe_t$ (alveolar concentration of carbon monoxide at time t). The computer takes the inspired volume measurement (Vi) and values for alveolar volume (Va) according to:

$$Va = Vi\,(ATPS) \times (FiHe/FaHe_t) \times STPD,$$

where ATPS and STPD are, respectively, atmospheric temperature and pressure and pressure saturated and standard temperature pressure dry. Alveolar Co is computed according to:

$$FaCO_o = FiCO \times (FaHe_t/FiHe).$$

Then, DLCO is computed as:

$$DLCO_{SB} = Va(STPD) \times CO/t \times 1/P_{B-47} \times L_n\,(FaCO_o/FaCO_i)$$

where $P_B$ equals barometric pressure and t equals time after washout volume.

FIG. 4 is a chart plotted in terms of sequential real time. Many of the systems components have two states (OP.; open, or CL., closed) that are effectively controlled by the computer program. Across the top of the chart are listed system functions located relative to the sequence in which they occur. First, for example, is the flush/calibrate period. In the first period, the instrumentation is calibrated by opening demand valve 16 and flushing the sample chamber 10 with the DLCO or other test gas to establish standards of relative levels of the gas constituents to be compared. During the next period, the patient procedure shown at the bottom of the chart is introduced. There follows a period for analysis, after which there is a period during which the chamber is again flushed by gas, then a period during which the chamber is flushed by air. Thereafter, the cycle repeats upon demand.

During the first flush calibrate period, the demand valve opens to a flush or steady state rate rather than a demand rate of test gas represented by (OP.) open on demand. During this period, the exhaust valve 22' is closed and the pneumotach valve 21' and mouthpiece valve 44' are open. The rebreathe valve 46' is also open and the turbine 40' is turned off. The pneumotach 20' is activated to measure the flow and the helium sensor 28'-30' is turned on, as is the $CO_2$ sensor 32'-36'. The CO sensor 24' is on the entire time. It will be observed that the sensors are left on longer than the full period of the flush so that the test gas can accumulate in the chamber. Thereafter, the valves close and the calibration procedure can continue. The computer calibrates the gas sensors.

When the flush/calibrate period is terminated, the patient procedure is begun. The patient at the mouthpiece 18' breathes normally with the mouthpiece valve 44' closed but with the rebreathe valve 46' open. At a signal, the patient breathes out as much as he is able, to a residual volume level in the lungs. At this point, the mouthpiece valve 44' is opened, the rebreathe valve 46' is closed and pneumotach valve 21' is opened. In the FIG. 1 version, the four-way valve 12 is placed in its solid line position so that the mouthpiece is attached to the DLCO gas supply and the patient breathes as deeply as possible, filling his lungs to capacity. At this point, the mouthpiece valve is closed briefly, for a ten second period, to allow the gas interchange to take place in the patient's lungs. After ten seconds, the mouthpiece valve 44 is reopened, as is the exhaust valve, and the pneumotach valve 21 remains open to measure the washout volume as the patient breathes out. Upon the measurement of a predetermined volume, the pneumotach valve 21 is closed, the exhaust valve 22 is closed, the mouthpiece valve 44 is closed and the rebreath valve 46 is opened. At this stage, the contents of the chamber is unable to escape in any direction and the chamber is effectively closed so that the turbine is turned on to thoroughly mix the gases for a predetermined brief period, following which the helium sensor and the carbon dioxide sensor are turned on for the analysis period. During this period, measurements are completed by the sensors in the chamber and, through the system illustrated in FIG. 3, provide data to the computer for calculation of the various parameters such as constituent gases. Thereafter, the demand valve 16 floods the system with gas for a gas flush and the mouthpiece valve, the rebreathe valve, the pneumotach valve are all open. The demand valve is then closed during an air flush and the exhaust valve is opened at this time. The mouthpiece and rebreathe valves remain open and the turbine is turned on to aid in the air flush. The pneumotach valve is also left open.

The present invention has been described in terms of two systems and the method of using those systems. It will be understood by those skilled in the art that the systems themselves can be varied and certainly the process used with the systems can be very substantially modified. Different constituent gases may be used or the proportions may be changed in making various tests. The procedures may also vary and the programming controlling the valves and other components of the system may be modified for that purpose.

For instance, a patient practice maneuver could be added prior to the "Flush/Calibrate" procedure. The patient would do the DLCO Breath hold maneuver without the DLCO test gas in his lungs, following which he would empty his lungs into the sample chamber with the appropriate valve action. This sample would then be used for two purposes. First, the gas sensors would be set to "zero" in this sample mixture. Moisture and $CO_2$ would then be "zeroed out" as interferences with the sound signals. Secondly, the range of the CO sensor would be switched from high range to low range (one-tenth original range) by the computer through a parallel resistor in the CO amplifier circuit. This allows the measurement of low levels of CO in the patient's breath which can be converted by the computer to percent carboxyhemoglobin. This measurement can be automatically applied by the computer as a correction to the DLCO calculation.

The pneumotach and its electronics can operate independently of the DLCO system and spirometric measurements can be made with the pneumotach connected to the sample chamber as shown, that is without changing the connections of the pneumotach to the sample chamber. The rebreath valve would be closed. The system of FIG. 1 would have the 4-way valve in the solid line position with the pneumotach, mouthpiece and exhaust valves open. In the system of FIG. 2, the mouthpiece, pneumotach and exhaust valves would be open. The pneumotach electronics would be connected to the computer which would make the standard spirometry calculations and reports.

Figure 5:
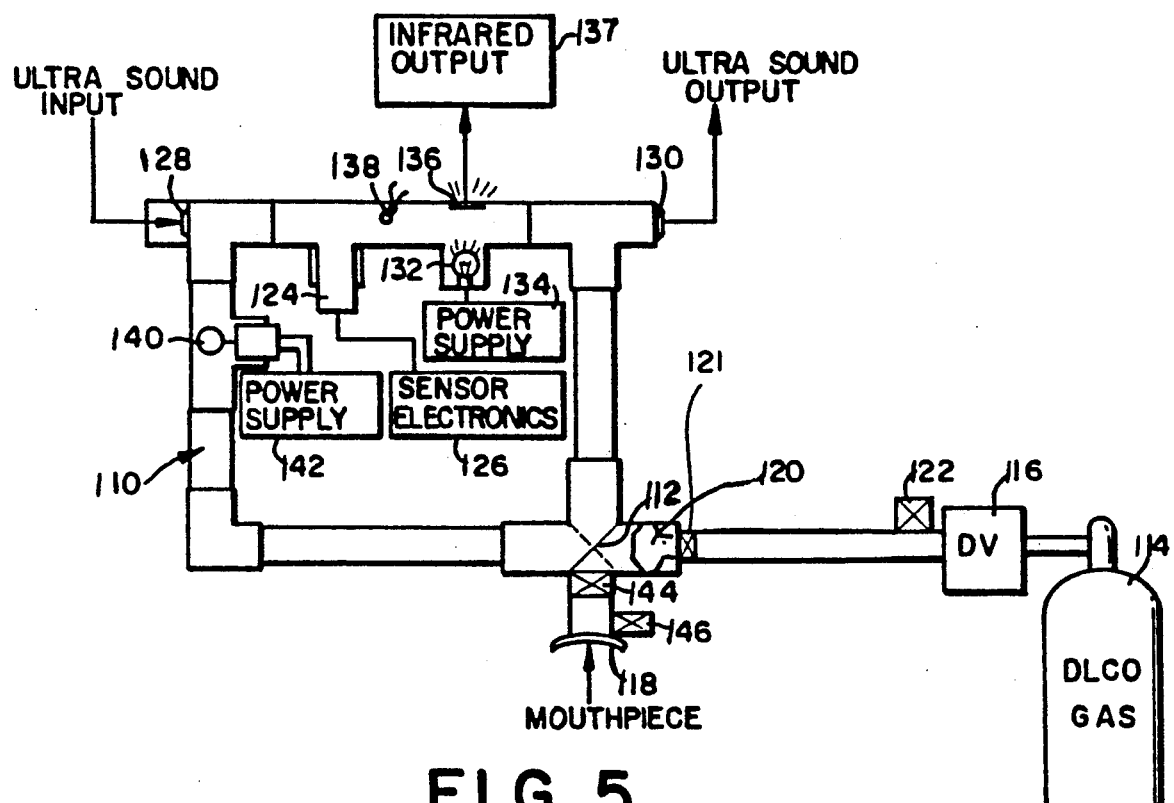
FIG. 5 is a similar view of the preferred form of the apparatus in FIG. 1 wherein the gas volume measuring device is located within the sample chamber.
Figure 6:
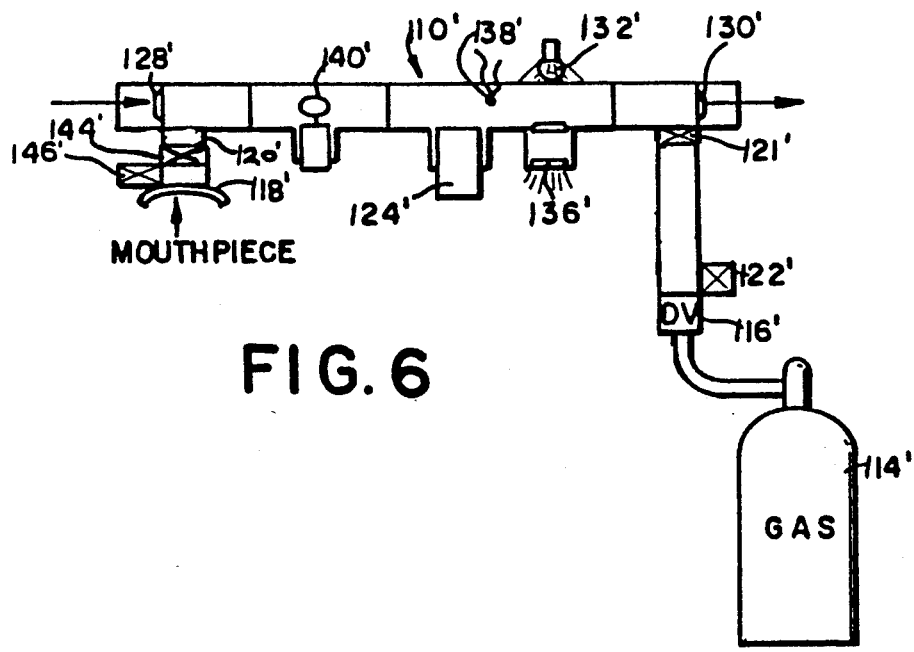
FIG. 6 is a similar view of another preferred form of the apparatus in FIG. 2 wherein the gas volume measuring device is located within the sample chamber.

A pneumotach or other volume measuring device could be located inside the sample chamber as shown in FIG. 5 and 6 to reduce the size of the whole system. In other respects FIG. 5 corresponds to FIG. 1 and FIG. 6 to FIG. 2 and corresponding parts have been given corresponding number designators with a "1" prefix as a hundreds digit. In fact volume measuring means can be located anywhere in the flow path between the mouthpiece valve and the exhaust valve. In the closed loop configuration of FIG. 5, the pneumotach could be located in or near the port of the four-way valve between the mouthpiece valve 144 and the pneumotach valve 121. In the linear configuration of FIG. 6, the gas volume measuring device could be located at either end or in the middle between the mouthpiece valve 144 and the pneoumtach valve 121.

The appended claims are intended to describe the system in broad terms. These claims are not intended to be limited to the systems actually described and shown as examples or to methods described, but should be interpreted to the broadest scope of their language.

I claim:

1. An apparatus for determining the various parameters related to the interaction of human lungs with one or more specified gases, comprising:
    a sample chamber;
    means within the chamber for sensing the gaseous components of the contents of the chamber;
    mixing means within the chamber for mixing the gaseous components of the contents of the chamber;
    a mouthpiece connected into said sample chamber for input of gases expired from the lungs of a patient under test;
    a test gas input connection attached at one end to the sample chamber and having means for connection with a source of standard test gas containing a predetermined concentration of one or more specified gases and valve means, including a demand valve, for allowing test gas to flow from the source through the sample chamber to the mouthpiece by its own pressure or on demand when the patient inspires through the mouthpiece;

mouthpiece valve means between the mouthpiece and the sample chamber for opening to enable the standard test gas to flow to the mouthpiece through at least a portion of the sample chamber, closing entirely for a predetermined breath hold period and then opening to enable expired gases to be breathed out into the sample chamber;

rebreath valve means between the mouthpiece and the mouthpiece valve means for connecting the mouthpiece to the atmosphere to allow normal breathing by the patient whereby the air inspired and the gases expired do not come from or go into the sample chamber when the rebreath valve means is open and the mouthpiece valve means is closed;

a gas volume measuring device between the test gas input connection and the sample chamber to measure the gas volume entering and exiting the sample chamber;

an exhaust valve between the gas volume measuring device and the test gas input connection to control exit of gases from the sample chamber; and pneumotach valve means between the sample chamber and the exhaust valve for allowing connection of the chamber to the exhaust valve, whereby, by opening and closing the mouthpiece, rebreath and pneumotach valve means and exhaust valve, sequential portions of the expired gases can pass through the exhaust valve, be trapped and held in the chamber for mixing and measurement of its gaseous constituents by the mixing and sensing means within the chamber, respectively, and be passed to the atmosphere without entering the chamber, so that in addition to gas volume measurement as the gases leave the chamber, measurement may be made of expired gaseous constituents related to lung effectiveness using the sensing means within the chamber.

2. The apparatus of claim 1 in which the test gas includes a predetermined concentration of carbon monoxide and the sensing means includes a carbon monoxide sensor to measure the quantity of carbon monoxide present in the contents of the sample chamber.

3. The apparatus of claim 1 in which the sensing means includes means for measuring the quantity of carbon dioxide present in the contents of the sample chamber.

4. The apparatus of claim 1 in which the test gas includes a predetermined concentration of helium and the sensing means includes helium gas measurement means to measure the quantity of helium present in the contents of the sample chamber.

5. The apparatus of claim 1 in which the test gas contains predetermined concentrations of both carbon monoxide and helium and the sensing means includes means for measuring the quantities of carbon monoxide and helium as well as carbon dioxide present in the contents of the sample chamber.

6. The apparatus of claim 5 in which the means for measuring helium include an ultrasound generator and an ultrasound detector spaced a fixed distance apart to measure the amount of helium in the sample chamber by its effect upon sound propagation between the ultrasound generator and the ultrasound detector.

7. The apparatus of claim 1 in which the chamber is configured as a closed loop with four-way valve means, having two alternative positions, located therein to enable in the first position for introduction of the expired gases from the mouthpiece into and through substantially the entire loop including the portion having the sensing means therein and in the second position for introduction of the standard test gas through the sample chamber to the mouthpiece without passing through the portion having the sensing means therein.

8. The apparatus of claim 7 in which temperature sensing means is provided in the vicinity of the means for sensing the gaseous components of the contents of the chamber.

9. The apparatus of claim 1 in which the sample chamber defines a substantially linear path between the mouthpiece valve means and the pneumotach valve means and said mixing means and said sensing means are located along said substantially linear path.

10. The apparatus of claim 1 in which the gas volume measuring device is located between the mouthpiece valve means and the pneumotach valve means.

11. A method of measuring the diffusing capacity of lungs using an apparatus as claimed in claim 1, comprising the following steps:

connecting the means for connection with a source of standard test gas;

connecting the mouthpiece to the mouth of a patient;

opening the rebreath valve means and closing the mouthpiece valve means and having the patient expire to residual volume;

closing the rebreath valve means and opening the mouthpiece and pneumotach valve means and having the patient inspire so that the test gas will flow through the volume measuring device, sample chamber and mouthpiece;

closing the mouthpiece and pneumotach valve means thereby closing the sample chamber off from the patient and the remainder of the apparatus for a predetermined period;

opening the mouthpiece and pneumotach valve means and having the patient expire through the mouthpiece, the mouthpiece valve means, the sample chamber, the pneumotach valve means and the volume measuring device;

closing the mouthpiece and pneumotach valve means thereby closing the sample chamber off from the mouthpiece and exhaust valve and retaining a sample of expired gases in the sample chamber after a predetermined volume of expired gases has passed through the volume measuring device;

mixing the expired gas sample and measuring the gaseous constituents of the contents of the sample chamber by said mixing and sensing means, respectively, within the sample chamber; and opening the rebreath valve means and having the patient expire the balance of the expired gases to the atmosphere without entering the sample chamber.

12. An apparatus for determining the various parameters related to the interaction of human lungs with one or more specified gases, comprising:

a sample chamber;

means within the chamber for sensing the gaseous components of the contents of the chamber;

mixing means within the chamber for mixing the gaseous components of the contents of the chamber;

a mouthpiece connected into said sample chamber for input of gases expired from the lungs of a patient under test;

a test gas input connection attached at one end to the sample chamber and having means for connection with a source of standard test gas containing a predetermined concentration of one or more specified gases and valve means, including a demand valve, for allowing test gas to flow from the source through the sample chamber to the mouthpiece by its own pressure or on demand when the patient inspires through the mouthpiece;

mouthpiece valve means between the mouthpiece and the sample chamber for opening to enable the standard test gas to flow to the mouthpiece through at lest a portion of the sample chamber, closing entirely for a predetermined breath hold period and then opening to enable expired gases to be breathed out into the sample chamber;

rebreath valve means between the mouthpiece and the mouthpiece valve means for connecting the mouthpiece to the atmosphere to allow normal breathing by the patient whereby the air inspired and the gases expired do not come from or go into the sample chamber when the rebreath valve means is open and the mouthpiece valve means is closed;

a gas volume measuring device between the test gas input connection and the mouthpiece to measure the gas volume entering and exiting the sample chamber; and a pneumotach valve means separated from the mouthpiece valve means by at least the sample chamber for closing off the sample chamber for preventing flow out of the sample chamber or into the sample chamber;

an exhaust valve between the rest of the apparatus and the test gas input connection to control exit of gases from the sample chamber, whereby, by opening and closing the mouthpiece, pneumotach and rebreath valve means and exhaust valve, sequential portions of the expired gases can pass through the exhaust valve, be trapped and held in the chamber for mixing and measurement of its gaseous constituents by the mixing and sensing means within the chamber, respectively, so that in addition to gas volume measurement, measurement may be made of expired gaseous constituents related to lung effectiveness using the sensing means within the chamber.

13. The apparatus of claim 12 in which the test gas includes a predetermined concentration of carbon monoxide and the sensing means includes a carbon monoxide sensor to measure the quantity of carbon monoxide present in the contents of the sample chamber.

14. The apparatus of claim 12 in which the sensing means includes means for measuring the quantity of carbon dioxide present in the contents of the sample chamber.

15. The apparatus of claim 12 in which the test gas includes a predetermined concentration of helium and the sensing means includes helium gas measurement means to measure the quantity of helium present in the contents of the sample chamber.

16. The apparatus of claim 12 in which the test gas contains predetermined concentrations of both carbon monoxide and helium and the sensing means includes means for measuring the quantities of carbon monoxide and helium as well as carbon dioxide present in the contents of the sample chamber.

17. The apparatus of claim 16 in which the means for measuring helium include an ultrasound generator and an ultrasound detector spaced a fixed distance apart to measure the amount of helium in the sample chamber by its effect upon sound propagation between the ultrasound generator and the ultrasound detector.

18. The apparatus of claim 12 in which the chamber is configured as a closed loop with four-way valve means, having two alternative positions, located therein to enable in the first position for introduction of the expired gases from the mouthpiece into and through substantially the entire loop including the portion having the sensing means therein and in the second position for introduction of the standard test gas through the sample chamber to the mouthpiece without passing through the portion having the sensing means therein.

19. The apparatus of claim 18 in which temperature sensing means is provided in the vicinity of the means for sensing the gaseous components of the contents of the chamber.

20. The apparatus of claim 12 in which the sample chamber defines a substantially linear path between the mouthpiece valve means and the pneumotach valve means and said mixing means and said sensing means are located along said substantially linear path.

21. The apparatus of claim 12 in which the gas volume measuring device is located between the mouthpiece valve means and the pneumotach valve means.

22. A method of measuring the diffusing capacity of lungs using an apparatus as claimed in claim 14, comprising the following steps:

connecting the means for connection with a source of standard test gas;

connecting the mouthpiece to the mouth of a patient;

opening the rebreath valve means and closing the mouthpiece valve means and having the patient expire to residual volume;

closing the rebreath valve means and opening the mouthpiece and pneumotach valve means and having the patient inspire so that the test gas will flow through the volume measuring device, sample chamber and mouthpiece;

closing the mouthpiece and pneumotach valve means thereby closing the sample chamber off from the patient and the remainder of the apparatus for a predetermined period;

opening the mouthpiece and pneumotach valve means and having the patient expire through the mouthpiece, the mouthpiece valve means, the sample chamber, the pneumotach valve means and the volume measuring device;

closing the mouthpiece and pneumotach valve means thereby closing the sample chamber off from the mouthpiece and exhaust valve and retaining a sample of expired gases in the sample chamber after a predetermined volume of expired gases has passes through the volume measuring device;

mixing the expired gas sample and measuring the gaseous constituents of the contents of the sample chamber by said mixing and sensing means, respectively, within the sample chamber; and opening the rebreath valve means and having the patient expire the balance of the expired gases to the atmosphere without entering the sample chamber.

23. A method of measuring the diffusing capacity of lungs using an apparatus as claimed in claim 14, comprising the following steps:
- connecting the means for connection with a source of standard test gas;
- connecting the mouthpiece to the mouth of a patient;
- opening the rebreath valve means and closing the mouthpiece valve means and having the patient expire to residual volume;
- closing the rebreath valve means and opening the mouthpiece and pneumotach valve means and having the patient inspire so that the test gas will flow through the volume measuring device, sample chamber and mouthpiece;
- closing the mouthpiece and pneumotach valve means thereby closing the sample chamber off from the patient and the remainder of the apparatus for a predetermined period;
- opening the mouthpiece and pneumotach valve means and having the patient expire through the mouthpiece, the mouthpiece valve means, the sample chamber, and the volume measuring device;
- closing the mouthpiece, pneumotach and exhaust valve means thereby closing the sample chamber off from the mouthpiece and retaining a sample of expired gases in the sample chamber after a predetermined volume of expired gases has passed through the volume measuring device; and
- mixing the expired gas sample and measuring the gaseous constituents of the contents of the sample chamber by said mixing and sensing means, respectively, within the sample chamber.

\* \* \* \* \*

UNITED STATES PATENT AND TRADEMARK OFFICE
CERTIFICATE OF CORRECTION

PATENT NO. : 5,022,406

DATED : June 11, 1991

INVENTOR(S) : Harold W. Tomlinson

It is certified that error appears in the above-identified patent and that said Letters Patent is hereby corrected as shown below:

Column 7, line 47, "4a" should be --40a--.

Column 9, line 52, "open" should be --on--.

Column 13, line 13, "lest" should be --least--.

Column 14, line 31, "14" should be --12--.

Column 15, line 2, "14" should be --12--.

Signed and Sealed this

Second Day of March, 1993

Attest:

STEPHEN G. KUNIN

*Attesting Officer*   Acting Commissioner of Patents and Trademarks